United States Patent [19]

Beroff et al.

[11] Patent Number: 4,671,281

[45] Date of Patent: Jun. 9, 1987

[54] NON-METALLIC, BIO-COMPATIBLE HEMOSTATIC CLIPS (ONE PIECE WEDGE CLIP)

[75] Inventors: Howard Beroff; Robert B. Duncan, both of Bridgewater, N.J.

[73] Assignee: Ethicon, Inc., Somerville, N.J.

[21] Appl. No.: 612,510

[22] Filed: May 21, 1984

Related U.S. Application Data

[62] Division of Ser. No. 416,824, Sep. 13, 1982.

[51] Int. Cl.⁴ .............................................. A61B 17/00
[52] U.S. Cl. .................................... 128/346; 128/325
[58] Field of Search .................. 128/325, 326, 334 R, 128/334 C, 335, 346

[56] References Cited

U.S. PATENT DOCUMENTS 2,686,521  8/1954  Sheldon et al. .................. 128/346
3,579,751  5/1971  Jonckheere ....................... 128/346
4,416,266 11/1983  Baucom ............................ 128/325

Primary Examiner—C. Fred Rosenbaum
Assistant Examiner—C. W. Shedd
Attorney, Agent, or Firm—Robert L. Minier

[57] ABSTRACT

A sterile, hemostatic clip for use in occluding vessels. The clip comprises a pair of leg members resiliently connected at a pivot area disposed between the ends of said leg members. A wedge member is used to cause one portion of the leg members to diverge even more and consequently cause the opposing portions to converge and occlude a vessel placed therebetween.

2 Claims, 6 Drawing Figures

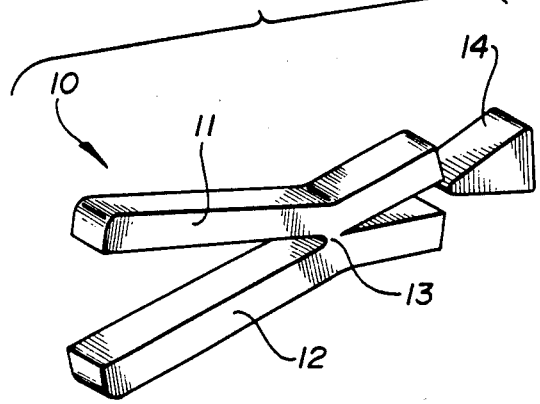
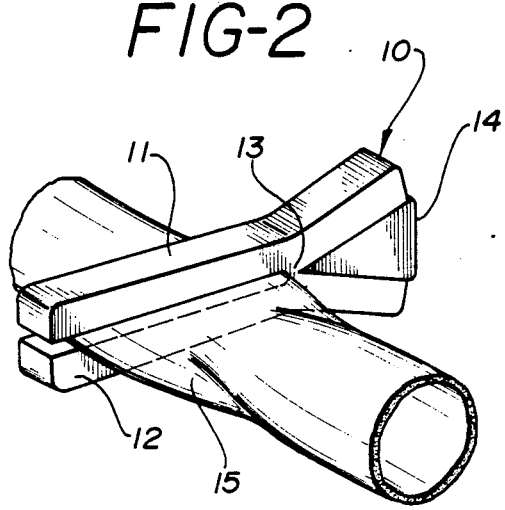
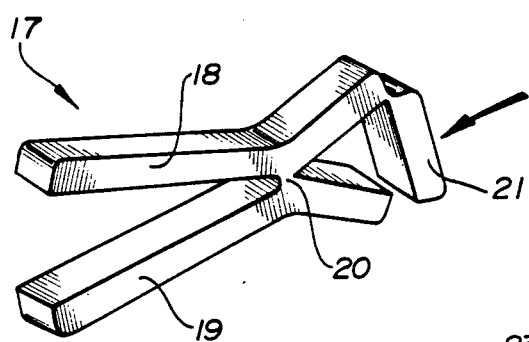
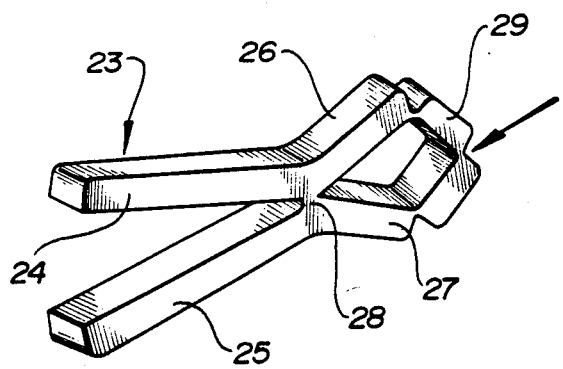

NON-METALLIC, BIO-COMPATIBLE HEMOSTATIC CLIPS (ONE PIECE WEDGE CLIP)

This is a division, of application Ser. No. 416,824, filed Sept. 13, 1982.

The present invention relates to hemostatic clips and more particularly to hemostatic clips fabricated from biocompatible polymeric materials which may be absorbable or non-absorbable in body tissue.

BACKGROUND OF THE INVENTION

In many surgical procedures, it is often necessary to ligate a pluarlity of vessels in the surgical site. The vessels may be severed downstream of the ligated portion. In some instances, the vessels may be ligated in spaced apart areas and the portion of the vessel between the ligations removed. The purpose of ligating vessels is to maintain the surgical site free from an excess of blood and reduce blood loss in the patient. Also, in certain surgical procedures where tumors and the like are to be removed, the tumor or organ may have to be separated from certain vessels. Before separating, the vessels are ligated. Once the blood vessel is completely shut off, hemostatis, that is, the natural physiological closing of the vessel so as to stop blood flow, will occur in several days depending on the vessel. The body, in the meantime, will continue to allow blood flow around the ligated area through appropriate capillaries and secondary vessels with the natural physiological function of the body enlarging these bypass vessels until adequate blood flow is obtained. Hence, when ligating the vessel, there should be positive stoppage of the blood flow in the main vessel. Failure to provide complete stoppage may cause blood loss in the patient and may also disrupt the natural hemostasis and concurrent manufacture of new paths of blood flow in the patient.

In the past, this closing of the vessel was usually accomplished using ligatures; i.e., filaments or threads which the doctor tied around the vessel to be closed. This is a time-consuming process and one wherein positive closing of the vessel is not always accomplished. In recent years, hemostatic clips have replaced ligatures in surgical procedures to close blood vessels and other fluid ducts. Very often these hemostatic clips are narrow U or V shaped strips formed of tantalum or stainless steel which are capable of being deformed and have sufficient strength to retain the deformation when clamped about a blood vessel. In recent years, a number of various types of clips made from bio-compatible polymeric materials have been developed. These are polymeric materials which are absorbable or non-absorbable in body tissue and various clip configurations are described in copending commonly assigned patent application Ser. Nos. 276,131 filed June 22, 1981, and 282,165 filed July 31, 1981. The polymeric clips should produce a positive closure about the vessel and be relatively easy to manipulate and handle by the nurse and surgeon. The clips should be smooth with gentle curves to reduce possible trauma in the surgical procedure. Also, it is preferred that the clip be readily and easily manufactured by simple well known techniques and, hence, be inexpensive to produce.

Our new clip is simple in construction and can be easily manipulated by the surgeon or nurse. Our new clip is also relatively inexpensive to manufacture.

SUMMARY OF THE PRESENT INVENTION

A sterile hemostatic clip for use in occluding vessels, said clip comprising a pair of leg members resiliently connected at a pivot area disposed between the ends of the leg members. The portions of the leg members extending from the pivot area in one direction diverging from each other and the portion of the leg members extending from the pivot area in the opposite direction also diverging from each other. The clip includes a wedge member adapted to fit between one of the diverging portions of said leg members to cause said portions to diverge even more and cause the opposite diverging portions to be urged together to occlude a vessel placed therebetween. In certain embodiments of the clip of the present invention, the wedge may be connected to one of the diverging legs while in other embodiments the wedge may be split so that a portion is connected to each of the diverging legs and the split wedge placed between the diverging portions. In the preferred embodiments of the present invention, the diverging portions used to occlude the vessel are longer than the diverging portions in which the wedge is placed.

BRIEF DESCRIPTION OF THE DRAWINGS

The present invention will be more fully described in conjunction with the accompanying drawings; wherein FIG. 1 is an enlarged view of a new clip of the present invention in the open position;

FIG. 2 is an enlarged perspective view of the clip of FIG. 1 in the closed position about a blood vessel;

FIG. 3 is an enlarged perspective view of another embodiment of a hemostatic clip in accordance with the present invention;

FIG. 4 is an enlarged perspective view of yet another embodiment of a hemostatic clip in accordance with the present invention;

DETAILED DESCRIPTION OF THE INVENTION

Figure 5:
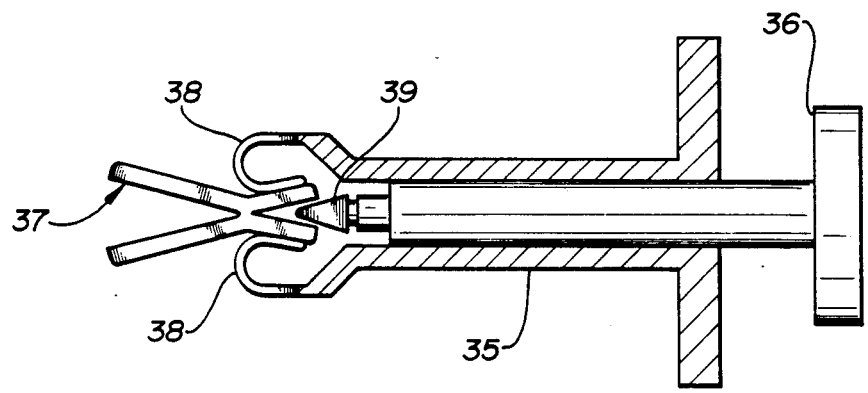
FIG. 5 is a side view in partial cross-section showing an instrument for applying the clips of the present invention.

Referring to the drawings, in FIG. 1 there is shown a clip 10 of the present invention in the open position. The clip comprises a pair of leg members 11 and 12 attached at a pivot area 13. The portion of the leg members extending in one direction from the pivot member diverge from each other while the portion of the leg members extending in the opposite direction from the pivot area also diverge from each other. In preferred embodiments of the clips of the present invention, the leg portions extending in one direction, which are those to be used to occlude the vessel, are greater in length than the leg portions extending in the opposite direction which are used to close the clip about the vessel. The clip includes a wedge shape member 14 to be placed between the shorter diverging leg portions. As is more clearly seen in FIG. 2 the longer diverging legs are placed on opposite sides of the vessel 15 to be occluded and the wedge inserted between the shorter diverging leg portions to cause these leg portions to diverge even more and consequently cause the longer diverging leg portions to be urged together to close the vessel.

In FIG. 3, there is shown another embodiment of the clip 17 of the present invention. Again, the clip 17 comprises a pair of leg members 18 and 19 connected at a resilient area 20. A portion of the leg members extend in one direction from the resilient area and diverge from each other while a portion of the leg members extend in the opposite direction from the resilient area and also diverge from each other. A wedge 20 or stuffing member is attached to the end of one of the shorter diverging leg portions. This member may be urged between the shorter diverging leg portions to cause them to part even further and close the longer diverging leg portions to occlude a vessel placed therebetween.

In the embodiment shown in FIG. 4, there is a clip 23 of the present invention with two longer diverging leg portions 24 and 25 and two shorter diverging leg portions 26 and 27. All of the leg portions are connected at the resilient area 28. In this embodiment, a member 29 with a section attached to each of the shorter diverging leg portions is placed between the shorter diverging leg portions. The member has a toggle like action. When the member is moved over dead center, the shorter diverging leg portions are pushed apart and close the longer diverging leg portions to occlude a vessel placed therebetween.

As may be seen in FIG. 5, one instrument that may be used for applying the clips of the present invention is similar to a hypodermic instrument in that it comprises a shell or syringe 35 and a plunger mechanism 36. At the end of the syringe the clip 37 is held in a pair of opposed jaws 38. If desired, these jaws may be urged together by suitable spring means to hold the clip in place. Disposed at the end of the plunger is the wedge shaped member 39. The jaws of the hypodermic instrument are placed adjacent the blood vessel so that the longer diverging leg portions of the clips are disposed on opposite sides of the vessel. The plunger or syringe is pushed forwardly or downwardly in the syringe inserting the wedge between the shorter diverging members, spreading them apart and closing the longer diverging members about the vessel. The jaws holding the clip are released, the instrument removed, and the clip left on the vessel in the closed position.

Figure 6:
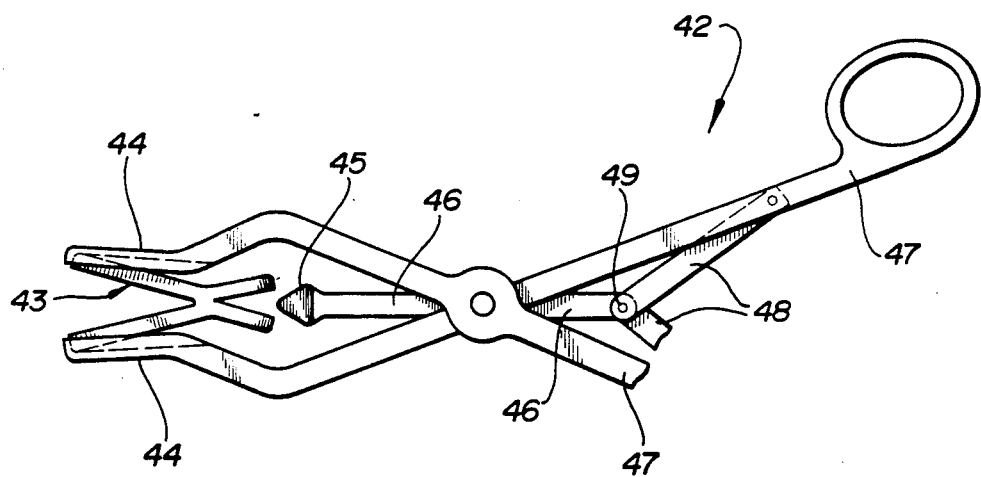
FIG. 6 is a side view depicting another instrument for applying the clips of the present invention.

In FIG. 6 there is shown another clip applying instrument that may be used with any of the clips previously described. The instrument 42 closes the clip around the vessel to be ligated, and at the end of the closing motion, pushes the wedge member between the shorter diverging legs, thereby locking the clip in the closed position. An open clip 43 is positioned in the grooved jaws 44 of the instrument. The wedge member 45 is positioned on the driver 46. The clip is positioned over the vessel to be ligated. The handles 47 are closed and the instrument jaws 44 close the clip. As the final closed position is reached linkage 48 pivots around pinned joint 49 and moves the driver 48 towards the clip pressing the wedge member 45 between the shorter diverging legs of the clip. The instrument may then be opened and removed leaving the clip in the closed and locked position about the vessel.

The clips of the present invention may be constructed in various sizes according to their intended function. Hemostatic clips are usually less than 6 millimeters in length and 1½ millimeters in width and have a vessel clamping surface of about 3 millimeters in length. The dimension of the clip may be reduced by about 50% for certain applications in microsurgery. Larger clips for special hemostatic applications may be about double the size of a typical hemostatic clip. The various sizes of the clips are preferably matched with individual appliers having jaws tailored to the size of the clip for best performance.

The clips of the present invention are most conveniently molded of biologically acceptable polymeric materials which may be absorbable or non-absorbable in body tissue. The preferred absorbable polymers and copolymers include those of glycolide, lactide, and poly(p)dioxanone. Preferred non-abosrbable polymers include nylon, polyester, and polypropylene. All of these materials have been demonstrated to be biologically acceptable when used as sutures or other implantable medical devices.

The clips of the present invention are sterilized by any of the well known sterilization techniques generally depending on the type of material used to manufacture the clip. Suitable sterilization techniques include heat or steam sterilization, radiation sterilization such as cobalt 60 irradiation or electron beam, ethylene oxide sterilization, and the like.

The clips of the present invention may be easily and economically manufactured by injection molding or other suitable molding techniques well known in the art.

Having now described the present invention and certain specific embodiments therein, it will be readily apparent to those skilled in the art that many variations and modifications may be made to the present invention without departing from the spirit and scope thereof.

What is claimed is:

1. A sterile, hemostatic clip for use in occluding vessels comprising a pair of leg members resiliently connected at a pivot area disposed between the ends of said leg members, the portions of said leg members extending from the pivot area in one direction diverging from each other and the portions of said leg members extending from the pivot area in the opposite direction diverging from each other, a wedge member adapted to fit between one of the diverging portions of said leg members to cause said portions to diverge even more and consequently cause said opposite diverging portions to be urged together to occlude a vessel placed therebetween, said wedge member being attached to at least one of said leg members by flexible connection means.

2. The sterile hemostatic clip according to claim 1 wherein the wedge member is split and a portion of the wedge member is attached to each leg of said one of the diverging portions.

* * * * *